(12) United States Patent
Richter

(10) Patent No.: US 9,060,851 B2
(45) Date of Patent: Jun. 23, 2015

(54) COVERING FOR AN ENDOPROSTHETIC DEVICE AND METHODS OF USING FOR ANEURYSM TREATMENT

(75) Inventor: Jacob Richter, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 469 days.

(21) Appl. No.: 12/540,649

(22) Filed: Aug. 13, 2009

(65) Prior Publication Data
US 2009/0306759 A1    Dec. 10, 2009

Related U.S. Application Data

(62) Division of application No. 11/367,530, filed on Mar. 3, 2006.

(60) Provisional application No. 60/673,304, filed on Apr. 19, 2005.

(51) Int. Cl.
*A61F 2/06* (2013.01)
*A61F 2/07* (2013.01)
(Continued)

(52) U.S. Cl.
CPC ................. *A61F 2/07* (2013.01); *A61B 5/0215* (2013.01); *A61B 5/6882* (2013.01); *A61F 2002/075* (2013.01); *A61F 2002/823* (2013.01); *A61F 2250/0023* (2013.01); *A61F 2/90* (2013.01)

(58) Field of Classification Search
CPC .................................................. A61F 2002/823
USPC .......................................... 623/1.3, 1.39, 1.4
See application file for complete search history.

(56) References Cited

U.S. PATENT DOCUMENTS 4,647,416 A *  3/1987  Seiler et al. ................... 264/118
4,743,252 A     5/1988  Martin, Jr.
(Continued)

FOREIGN PATENT DOCUMENTS

EP    0 815 806 B1    3/2004
EP    1 543 798 A     6/2005
(Continued)

OTHER PUBLICATIONS

Michael A. Burbelko, Stent-Graft Placement for Wide-Neck Aneurysm of the Vertebrobasilar Junction, Apr. 2004, American Journal of NeuroRadiology 25:pp. 608-610.*
(Continued)

*Primary Examiner* — Thomas J Sweet
*Assistant Examiner* — Brian Dukert
(74) *Attorney, Agent, or Firm* — Cadwalader, Wickersham & Taft LLP

(57) ABSTRACT

The present invention relates to covered endoprosthetic devices. Covered endoprosthetic devices comprise an endoprosthesis and a sheath. The sheath comprises a central portion and outer portions, wherein the central portion preferentially restricts or causes a restriction of blood flow. Blood flow can be reduced by the central portion of the sheath by varying the permeability of the sheath or by having projections on the sheath that slow blood flow. Permeability may be provided by perforations or holes in the material of the sheath or by varying the polymer structure that makes up the sheath itself. The outer portions of the sheath do not substantially reduce blood flow. Methods of using sheath-covered endoprosthetic devices of the invention to treat aneurysms, especially aneurysms in proximity to small perforator vessels or arteries, are also encompassed.

15 Claims, 11 Drawing Sheets

(51) Int. Cl.
    *A61B 5/0215*     (2006.01)
    *A61B 5/00*     (2006.01)
    *A61F 2/82*     (2013.01)
    *A61F 2/90*     (2013.01)

(56) References Cited

U.S. PATENT DOCUMENTS

| | | | |
|---|---|---|---|
| 5,769,884 A * | 6/1998 | Solovay | 623/1.13 |
| 5,951,599 A * | 9/1999 | McCrory | 606/108 |
| 6,214,039 B1 | 4/2001 | Banas et al. | |
| 6,258,115 B1 | 7/2001 | Dubrul | |
| 6,309,367 B1 | 10/2001 | Boock | |
| 6,319,278 B1 | 11/2001 | Quinn | |
| 6,613,078 B1 | 9/2003 | Barone | |
| 6,730,119 B1 | 5/2004 | Smalling | |
| 6,846,316 B2 | 1/2005 | Abrams | |
| 7,220,276 B1 * | 5/2007 | Williams et al. | 623/1.47 |
| 7,972,628 B2 * | 7/2011 | Ratner et al. | 424/499 |
| 2002/0052649 A1 | 5/2002 | Greenhalgh | |
| 2002/0123790 A1 | 9/2002 | White et al. | |
| 2003/0130718 A1 * | 7/2003 | Palmas et al. | 623/1.12 |
| 2003/0130720 A1 | 7/2003 | DePalma et al. | |
| 2004/0039441 A1 * | 2/2004 | Rowland et al. | 623/1.42 |
| 2005/0154453 A1 | 7/2005 | Hunter et al. | |
| 2005/0154454 A1 * | 7/2005 | Hunter et al. | 623/1.42 |
| 2007/0100430 A1 * | 5/2007 | Rudakov et al. | 623/1.13 |

FOREIGN PATENT DOCUMENTS

| | | |
|---|---|---|
| JP | H08-196643 | 8/1996 |
| JP | 2001-509412 | 7/2001 |
| JP | 2004-261567 | 9/2004 |
| WO | WO 99/02092 | 1/1999 |
| WO | WO 02/24247 A | 3/2002 |
| WO | WO 02/35988 A | 5/2002 |
| WO | WO 03/049600 A2 | 6/2003 |
| WO | WO 03/070125 | 8/2003 |
| WO | WO 2004/006807 A2 | 1/2004 |
| WO | WO 2004/019790 A1 | 3/2004 |

OTHER PUBLICATIONS

Office Actions and Response of related U.S. Appl. No. 11/367,530: Request for Continued Examination with Amendment and Response to Final Rejection dated Sep. 28, 2010; Advisory Action dated Sep. 10, 2010; Amendment and Response to Final Rejection dated Aug. 30, 2010; Final Rejection dated Jun. 28, 2010; Amendment and Response to the Non-Final Rejection with one-month Extenson of Time date Mar. 29, 2010; Non-Final Rejection dated Dec. 16, 2009; Request for Continued Examination with Amendment and Response to Final Rejection dated Sep. 22, 2009; Advisory Action dated Sep. 4, 2009; and Amendment and Response to Final Rejection dated Aug. 21, 2009.
International Search Report for corresponding International Application Serial No. PCT/IB06/00471, mailed Mar. 24, 2008.
Office Actions and Responses to Office Actions of co-pending parent U.S. Appl. No. 11/367,530: Final Rejection dated Jun. 22, 2009; Response to Election/Restriction Requirement dated Mar. 18, 2009; Restriction/Election Requirement dated Feb. 18, 2009; Response to Election/Restriction Requirement dated Nov. 18, 2008; Restriction/Election Requirement dated Oct. 20, 2008; Amendment and Response to Non-Final Office Action dated Jul. 8, 2008; and Non-Final Rejection dated Apr. 8, 2008.
Extended European Search Report from corresponding European Application No. EP 06727281 (EP 1 871 291 A) dated Jun. 5, 2009.
Extended European Search Report from corresponding EP Application No. 11181285.5-1526 dated Nov. 18, 2011, 6 pages.
Office Actions and Responses of related U.S. Appl. No. 11/367,530: Amendment and Response to Interview dated Jul. 30, 2012; Applicant Initiated Interview Summary dated Jul. 24, 2012; and Supplemental Response and Amendment dated Jul. 12, 2012.
Office Actions and Responses for related U.S. Appl. No. 11/367,530: Response to Final Rejection with Request for Continued Examination dated Jan. 9, 2014; and Final Rejection dated Oct. 9, 2013.
Office Actions and Responses for related U.S. Appl. No. 11/367,530: Non-Final Office Action dated Feb. 14, 2014.

* cited by examiner

COVERING FOR AN ENDOPROSTHETIC DEVICE AND METHODS OF USING FOR ANEURYSM TREATMENT

This application is a divisional of U.S. patent application Ser. No. 11/367,530, Mar. 3, 2006, and claims the benefit of priority of U.S. Provisional Application Ser. No. 60/673,304, filed Apr. 19, 2005, all of which are incorporated herein by reference in their entirety.

FIELD OF THE INVENTION

The present invention relates to a covering for endoprosthetic devices. Methods of using endoprosthetic devices covered by a sheath of the invention to treat aneurysms are also encompassed. The coverings preferentially restrict blood flow to the aneurysm while leaving surrounding areas substantially unaffected. In specific embodiments, aneurysms in proximity to small perforator vessels or arteries are treated using devices and methods of the invention.

BACKGROUND OF THE INVENTION

An aneurysm is a phenomenon in which the wall of a blood vessel, typically an artery, is abnormally dilated due to weakening of the vessel wall and a bulb or ball shaped space is created connected to the vessel by a neck. Depending upon where in the body the aneurysm is located, a ruptured aneurysm may be fatal.

Until recently, the main treatment of intracranial ruptured and unruptured aneurysms had been to expose the aneurysm in a surgical procedure and to clip the neck of the aneurysm using surgical clips. These open surgical procedures carry a significant degree of morbidity and mortality. Further, some intracranial aneurysms are inaccessible to open procedures due to their locations deep inside the brain tissue.

More recently, aneurysm repair devices have been used to prevent the aneurysm from getting larger and ultimately rupturing. One popular type of minimally invasive treatment is a detachable coil (DC) which is a wire that is packed into the aneurysm through a catheter and then detached from the catheter. The goal of packing enough mass of this wire into the aneurysm is to increase the resistance to flow into the aneurysm. The probability of aneurysm rupture is further reduced if the slow flow into the aneurysm cause the formation of a thrombus which excludes the aneurysm from even more flow. The many shortcomings of this approach include the unpredictable nature of the procedure (thus leaving a number of aneurysms exposed to significant flow), the high number of coils required (which adds to the length and cost of the procedure), and the possible embolization of coils into distal vessels (thereby occluding them). These problems are especially relevant during treatment of aneurysms with wide necks (e.g., aneurysms having a wide connection to the blood vessel).

Many practitioners have attempted to provide an endoprosthetic device for therapeutically treating aneurysms that does not require an open procedure and whose success is not dependent on the configuration of the aneurysm. For example, there have been a number of proposals for placement of an intraluminal graft bridging the aneurysm to isolate the aneurysmal sac from the active arterial duct. However, this method also occludes any small perforator arteries or vessel branches (both inlet and outlet branches) in the area of the aneurysm and thus causes loss of blood flow to the branches.

There is therefore a need in the art for an aneurysm repair device that has good and predictable aneurysm-sealing characteristics while having a minimal effect on the distal vessel as well as small branching vessels around the neck of the aneurysm.

SUMMARY OF THE INVENTION

The present invention relates to coverings for endoprosthetic devices. Such endoprosthetic devices comprise an endoprosthesis and a covered portion or sheath. The endoprosthesis is covered on all or part of its outer surface by a sheath that comprises a central portion and outer portions. The sheath preferentially restricts or causes a restriction of blood flow to the aneurysm while leaving blood flow to surrounding areas (e.g., small perforator vessels or arteries around the neck of the aneurysm) substantially unaffected. In one embodiment, blood flow to the aneurysm is restricted by varying the permeability of the sheath. Permeability (i.e., porosity) of the sheath may be provided by perforations or holes in the material of the sheath, polymer coatings on the sheath, by varying the polymer structure that makes up the sheath itself, or by directing differential cell growth on the sheath.

In a specific embodiment, the sheath comprises a central portion that is less permeable to blood flow than the outer portions. As a result, blood flow through the covered endoprosthesis can be controlled and varied as desired. The central portion of the sheath may be less permeable to blood flow than the outer portions of the sheath, for example, by having fewer and/or smaller perforations and/or a less porous structure and/or by having preferential cell growth than the outer portions.

In another embodiment, blood flow to the aneurysm is restricted by projections on the sheath. In a specific embodiment, the sheath comprises a central portion that has projections. The projections extend into the aneurysm through its neck. Projections on the sheath in areas not opposing the neck of the aneurysm are caught between the sheath and the wall of the vessel and thus not extended. The projections serve to slow blood flow into the aneurysm and thus may promote thrombosis. In this embodiment, the projections are 0.5 mm-5.0 mm in length. Preferably, the projections are longer than the diameter of any perforator vessel or artery in proximity to the aneurysm.

In another embodiment, the sheath comprises a central portion that has substantially the same permeability to blood flow as the outer portions. The permeability of the sheath is such that blood flow is allowed into areas (such as perforator vessels) that have an out-flow but is restricted to areas that do not have an out-flow (such as the aneurysm). In this embodiment, the sheath has a porosity in the range of 10-100 micrometers.

The sheath may be attached to the endoprosthetic device permanently or transiently. The sheath may be expandable such that, as an endoprothesis is delivered into the lumen of the sheath, the sheath will take on the exterior configuration of the endoprosthesis. The endoprothesis may be any endoprothesis known in the art. In preferred embodiments, the endoprosthesis is a stent.

The sheath may be generally cylindrical in shape and have a lumen therethrough. The variability in blood flow caused by the sheath may be in sections that extend around the entire circumference of the sheath. Alternatively, variability in blood flow caused by the sheath may be in sections that are confined to smaller areas that do not extend around the entire circumference of the sheath. In some embodiments, the sheath only has a central portion.

Methods of using the endoprosthetic device of the invention, e.g., to treat aneurysms, are also encompassed by the present invention. In such methods, the covered endoprosthetic device is placed in the lumen of the blood vessel or artery in the area of the aneurysm and is positioned such that the central portion of the sheath is facing the aneurysm. Thus, blood flow is reduced in the aneurysm. The reduced speed and amount of blood flow to the aneurysm may trigger a thrombosis which further excludes the aneurysm from blood pressure. This reduces the risk of aneurysm rupture.

Any aneurysm can be treated according to the methods of the invention. In one embodiment, the aneurysm is an intracranial aneurysm. More particularly, the intracranial aneurysm may be in proximity to one or more perforators. In embodiments where the aneurysm is in proximity to one or more perforators, blood flow obstruction to the perforators due to the sheath-covered endoprosthesis is minimized by 1) placement of the outer portion of the sheath facing the perforators such that the central section, e.g., the portion that restricts blood flow, is facing the neck of the aneurysm while the outer sections, e.g., the portions that do not substantially restrict blood flow, face the perforators or 2) covering the endoprosthesis with a sheath that allows flow into areas that have an out-flow but restricts flow to areas that do not have an out-flow. In this way, blood flow into the aneurysm is eventually decreased or eliminated without critically affecting blood flow to any perforator in proximity to the aneurysm.

DETAILED DESCRIPTION OF THE INVENTION

Figure 1A:
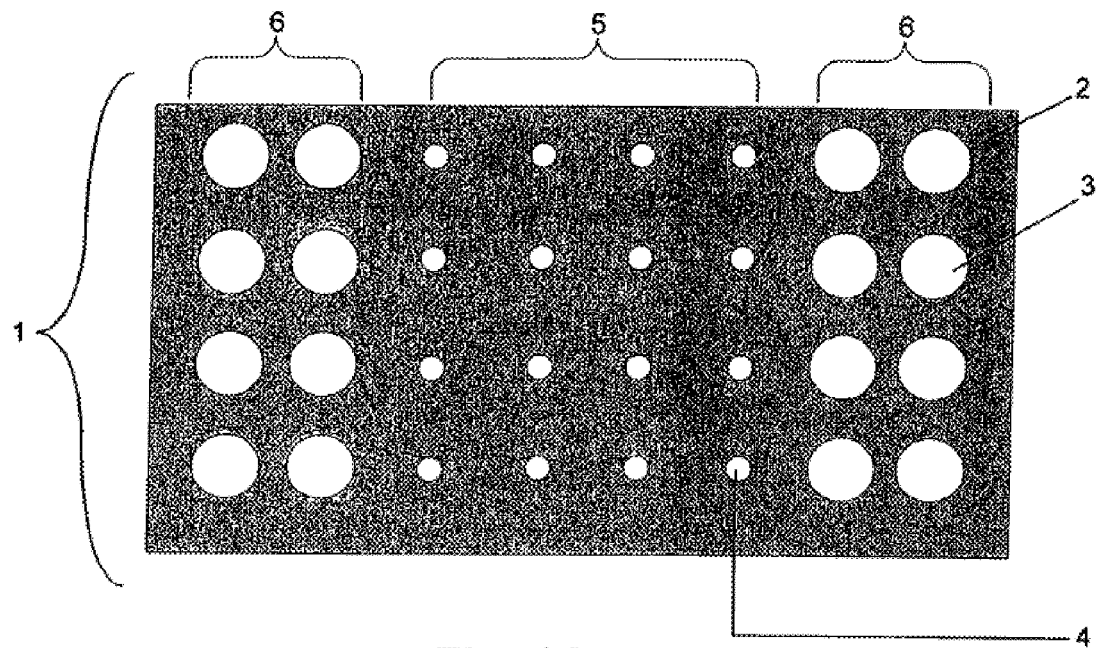
FIGS. 1A-1B are schematic views of a sheath 1 in one embodiment of the invention. In this embodiment, the size of the perforations is varied between the central portion 5 and the outer portions 6 of the sheath. The sections that dictate variability in blood flow permeability extend around the circumference of the sheath and along its entire length. The flattened sheath in (A) has been made into a cylinder in (B). The small perforations of the central portion 5 extend around the entire circumference of the sheath as can be seen in (B).

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

The covered endoprosthetic devices of the invention are covered with a sheath. The sheath preferentially restricts or causes a restriction of blood flow to the aneurysm while leaving blood flow to surrounding areas (e.g., small perforator vessels or arteries around the neck of the aneurysm) substantially unaffected. In one embodiment, blood flow to the aneurysm is restricted by varying the permeability of the sheath (e.g., see FIGS. 1-5 and 9). In another embodiment, blood flow to the aneurysm is slowed by projections from the sheath that may result in thrombosis (e.g., see FIG. 10).

A sheath of the present invention may cover all or a part of an endoprosthetic device. In some embodiments, the sheath comprises a central portion flanked by outer portions. In other embodiments, the sheath comprises only a central portion. The central portion of the sheath restricts or causes a restriction of blood flow to the aneurysm. This reduced blood flow to the aneurysm can be caused by the central portion having 1) a low permeability to blood flow (caused by, e.g., small or no perforations in the material of the sheath, polymer coatings on the sheath, the polymer structure of the material of the sheath itself, or cell growth on the sheath) or 2) projections that extend into the neck of the aneurysm. The outer portions of the sheath allow sufficient blood flow so that any perforator vessel or artery facing an outer portion will not be substantially affected. The outer portions may or may not allow the same amount of blood flow when compared to each other, however, the outer portions will preferably allow a greater amount of blood flow than the central portion.

In some embodiments, the central portion is uniform around the entire circumference of the sheath (see, e.g., FIGS. 1, 2, 4, 9, and 10). In other embodiments, the central portion is not uniform around the entire circumference of the sheath (see, e.g., FIGS. 3 and 5). In such embodiments, there is a section of the central portion that restricts or causes a restriction of blood flow which can be positioned opposite the neck of aneurysm. Other sections of the central portion that do not substantially restrict blood flow are positioned opposite small perforator vessels or arteries around the neck of the aneurysm without compromising blood flow to them. These sections of the central portion that do not substantially restrict blood flow may or may not have the same permeability to blood flow that the outer portions.

The sheath may also have multiple "central" portions, for example, when the sheath is intended to cover multiple aneurysms which are close enough in proximity to be covered with a single device. In such an embodiment, the central portions may be positioned to cover such aneurysms, while outer portions may preferably be located to surround the central portions. It is understood that many of the embodiments described herein may be adapted to accommodate multiple central portions.

The sheath may further include a proximal opening and a distal opening. In its non-distended configuration, the sheath may generally form a cylinder. The sheath may be attached to the endoprosthesis by any method known in the art, providing that the method of attachment is appropriate for the materials used to make the sheath and endoprosthesis. In one embodiment, an adhesive bond is used to attach the sheath to the endoprosthesis. Such a bond may be engineered to detach at any desired time or at a desired force. The adhesive bond may be formed with any medically approved adhesive.

In one embodiment, the endoprosthesis is a stent. Any stent can be covered by the sheath of the invention to make a sheath-covered stent. The skilled artisan is well aware of the many stents available in the art. Any such stent may be amenable to use in the instant invention. The stents may be self-expanding or may be balloon-expandable stents. Any method can be used to attach the sheath to the stent, providing that the method of attachment is appropriate for the materials used to make the stent and sheath. In one embodiment, the sheath is attached to the stent using an adhesive bond. The sheath may be attached to the stent permanently or transiently.

Figure 1B:
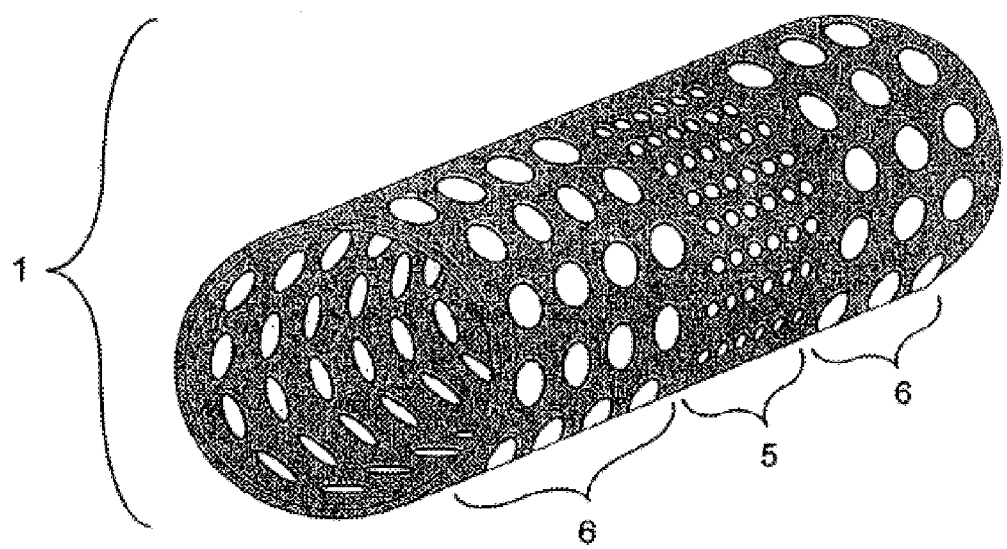

FIG. 1 illustrates the sheath 1 which makes the covered portion of the endoprosthetic device. The solid portion 2 of the sheath can be made of any material known in the art that has properties that allows the covered endoprosthetic device to be capable of getting to the affected area. For example, sheath 1 may be made of an elastomer or other highly compliant polymer. Such polymers may include latex, styrenic block copolymers such as SBS and SEBS made by Shell under trade name Kraton, polyether-ester block copolymers (COPE) for co-polyesters made by DuPont under the trade name of Hvtrel, thermoplastic polyamide elastomers (PEBA) made by Atochem under the trade name of Pebax, and thermoplastic polyurethane elastomer (TPUR) made by Dow under the trade name Pellathane, or thermoplastic polyolefin elastomers (TPOs). The materials may themselves be biocompatible or they may be plated with a biocompatible material. Additionally, the materials may or may not be biodegradable. Similarly, the sheath may be made of any textile, film or material such as DACRON, polyester, polyethylene terephthalate (PET), polytetrafluoroethylene (PTFE), or any other suitable material. Preferably the material is compliant.

In embodiments where the sheath has differential permeability, the differential permeability may be provided by the selection of specific materials to make up the sheath. Many permeable materials are known to the skilled artisan and their use in the sheath of the invention is encompassed herein. The terms permeability, porosity, and perforations (density thereof) are used interchangeably herein.

In some embodiments, the sheath 1 has perforations 3, 4 that allow some blood to flow through the sheath, i.e., porosity. Although circular perforations 3, 4 are shown in FIG. 1, the perforations in the sheath may be of any shape. The perforations in the sheath can be all of the same shape or they may be more than one shape. In the embodiment illustrated in FIG. 1, the size of the perforations vary in the sheath 1. For example, the central portion 5 of the sheath may have smaller perforations than those in the outer portions 6 (e.g., as shown by comparison of hole or perforation 4 with hole 3). Although the perforations in the central portion 5 and the outer portions 6 are shown in FIG. 1 as homogenous in size, the perforations in the sheath of the invention may be of varied size within a portion.

The perforations in the outer portions 6 are preferably large enough to allow sufficient blood flow through the sheath such that any perforator vessel or artery facing the outer portion would not be substantially affected. The outer portions 6 may or may not have the same size perforations when compared to each other, however, each of the outer portions will have an average hole size that is greater than the average hole size of the central portion.

The perforations in the central portion 5 are of a size and/or porosity to allow for some restricted permeability through the sheath such that an aneurysm facing a central portion will have reduced blood flow and pressure as compared to the amount of blood flow and pressure in the absence of the sheath. In this embodiment, other parts of the sheath contain larger perforations to provide more permeability. The size of the perforations can be empirically determined by the skilled artisan based on physiological factors such as type and size of the vessel and size/morphology of the aneurysm being treated.

In one embodiment, the porosity of the central portion is uniform around the entire circumference of the sheath. In a specific embodiment, depicted in FIG. 1, the sheath has a uniform porosity throughout the entire central portion. In another specific embodiment, a sheath has heterogeneous porosity in the central portion so long as the overall porosity of this portion is uniform around the entire circumference of the sheath.

Figure 2A:
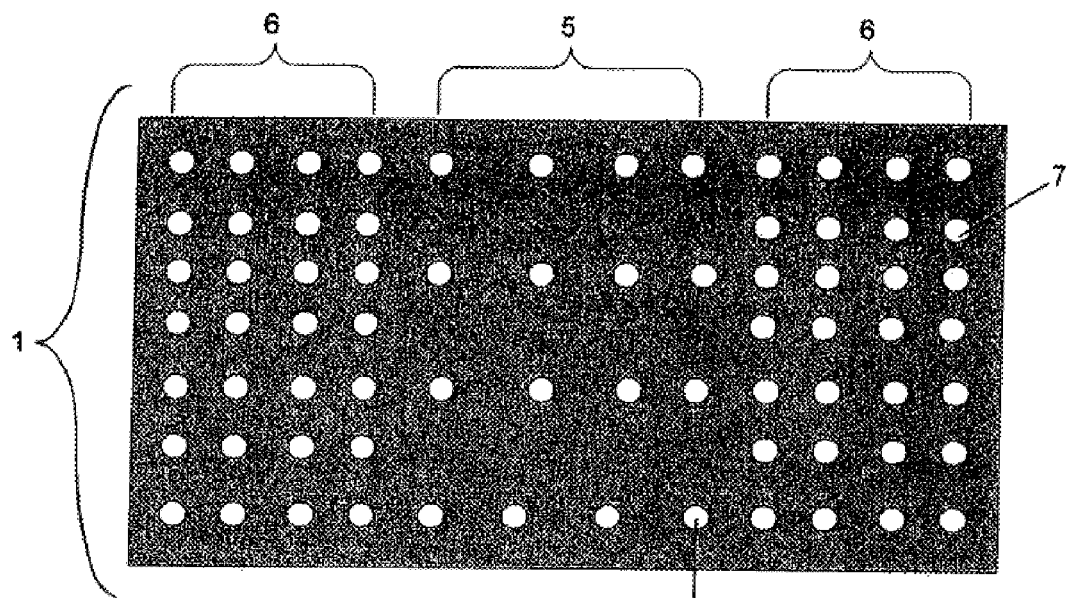
FIGS. 2A-2B are schematic views of another embodiment of the sheath 1 of the invention. Here, the number of perforations is varied between the central portion 5 and the outer portions 6 of the sheath. The sections that dictate variability in blood flow permeability extend around the circumference of the sheath and along its entire length. The flattened sheath in (A) has been made into a cylinder in (B). The less dense perforations of the central portion 5 extend around the entire circumference of the sheath as can be seen in (B).
Figure 2B:
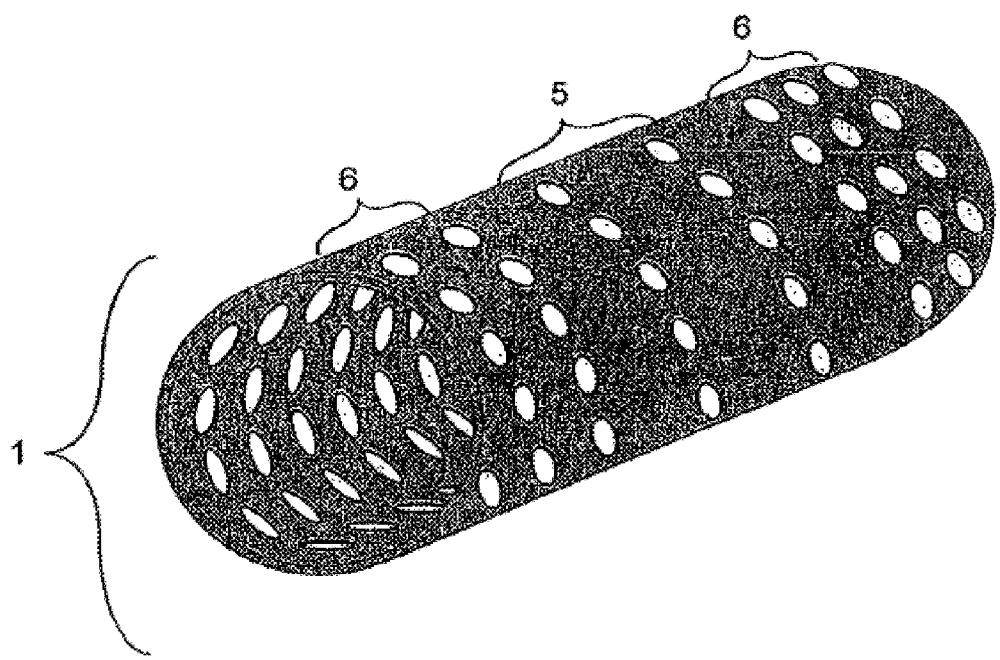

Another embodiment of the invention is illustrated in FIG. 2. In this embodiment, the sheath 1 has perforations 7, 8 to allow some permeability in the sheath. The perforations 7, 8 are less dense in the central portion 5 than in the outer portions 6. The density of perforations in the sheath is such that there is overall less permeability in the central portion than the outer portion of the sheath.

The density of the perforations in the outer portions 6 is high enough to allow sufficient blood flow so that any perforator vessel or artery facing an outer portion will not be substantially affected. The outer portions may or may not have the same density of perforations (i.e., porosity) when compared to each other, however, the outer portions will preferably have a porosity that is greater than the porosity of the central portion 5.

Although perforations 7, 8 are of the same size in FIG. 2, the perforations in the sheath may be of different sizes and/or shapes. In some embodiments, it may be preferable to combine the embodiments of FIGS. 1 and 2 to provide a sheath having a plurality of perforations of varying size in the outer portions, and fewer and/or smaller openings in the central portions of the sheath.

In another embodiment, the porosity of the central portion is uniform around the entire circumference of the sheath. In a specific embodiment, depicted in FIG. 2, the sheath has uniform-sized perforations in the central portion. In another specific embodiment, a sheath has heterogeneous-sized perforations in the central portion, however, the overall porosity of the central portion is uniform around the circumference of the sheath.

Figure 3A:
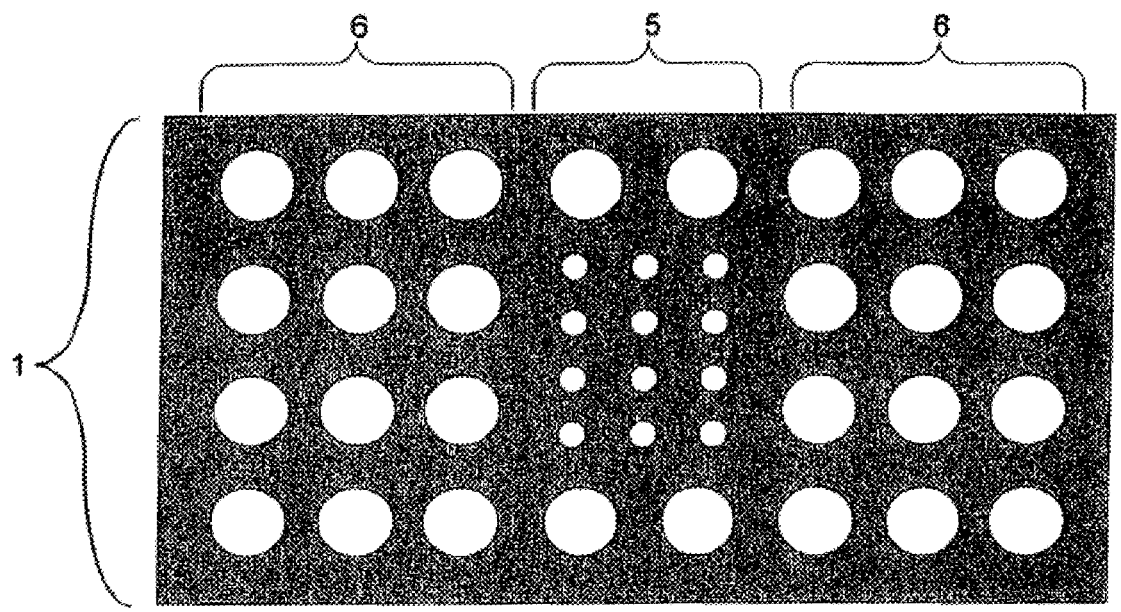
FIGS. 3A-3B are schematic views of another embodiment of the sheath 1 in another embodiment of the invention. In this embodiment, the size of the perforations is varied between the central portion 5 and the outer portions 6 of the sheath. The smaller perforations of the central portion 5 are confined to a region that is smaller than the size of the entire middle part of the sheath. The flattened sheath in (A) has been made into a cylinder in (B). The smaller perforations of the central portion 5 do not extend around the entire circumference of the sheath as can be seen in (B).
Figure 3B:
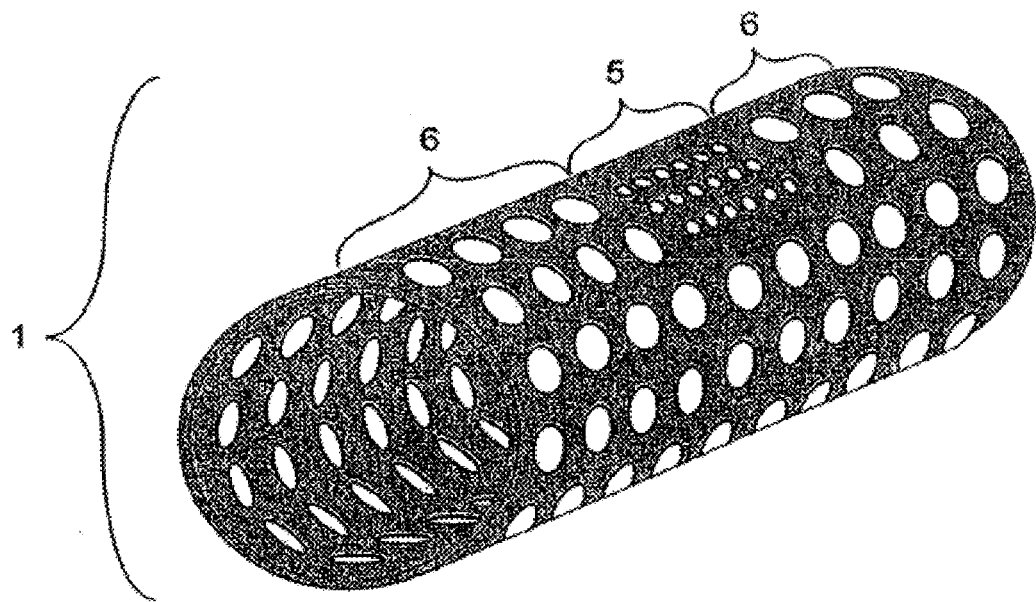

Another embodiment of the invention is illustrated in FIG. 3. In this embodiment, the sheath 1 has variable-sized perforations to allow variable permeability in the sheath. The central portion 5 has a decreased porosity than either of the outer portions 6. However, the porosity of the central portion 5 is not uniform around the entire circumference of the sheath in this embodiment. The region of decreased porosity in the central portion 5 is conferred by an area that has perforations that are smaller in size than those of the outer portions 6. This region is confined to an area that is smaller than the entire central portion of the sheath and thus does not continue around the entire circumference of the sheath. The remainder of the central portion has a porosity that is substantially similar to that of the outer portions.

Although FIG. 3 depicts a central portion with a region of decreased porosity conferred by the presence of an area of smaller perforations, any means may be used to decrease porosity. For example, the region of deceased porosity in the central portion can be conferred by having perforations that are less densely spaced than in the outer portions.

Figure 4A:
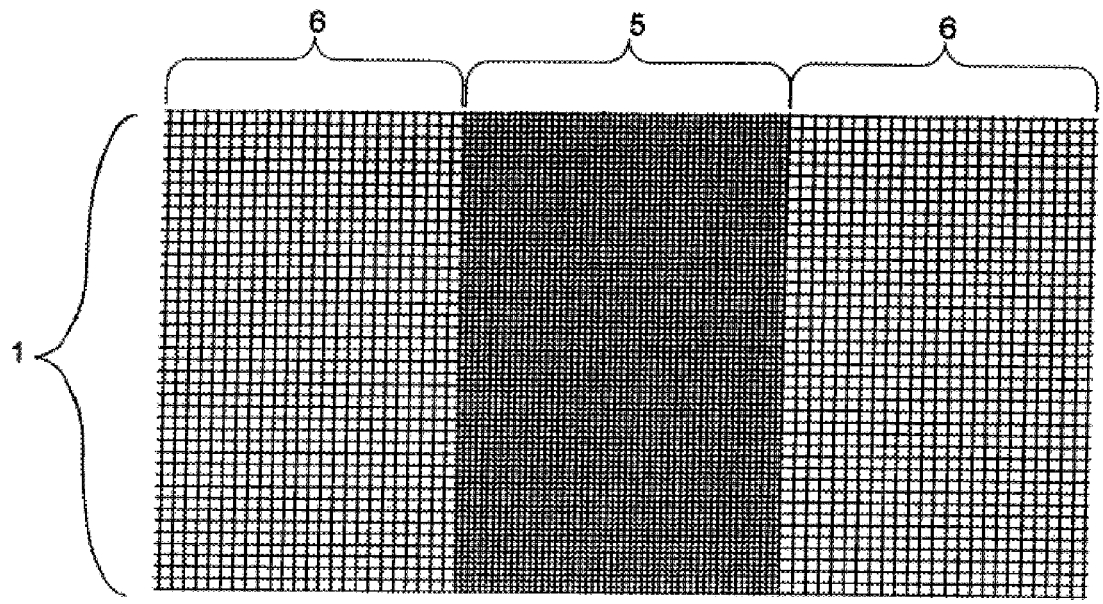
FIGS. 4A-4B are schematic views of a sheath 1 in another embodiment of the invention. In this embodiment, the porosity of the polymer structure that makes up the sheath itself is varied between the central portion 5 and the outer portions 6 of the sheath. The sections that dictate variability in blood flow permeability extend around the circumference of the sheath and along its entire length. The flattened sheath in (A) has been made into a cylinder in (B). The less permeable area of the central portion 5 extends around the entire circumference of the sheath as can be seen in (B).
Figure 4B:
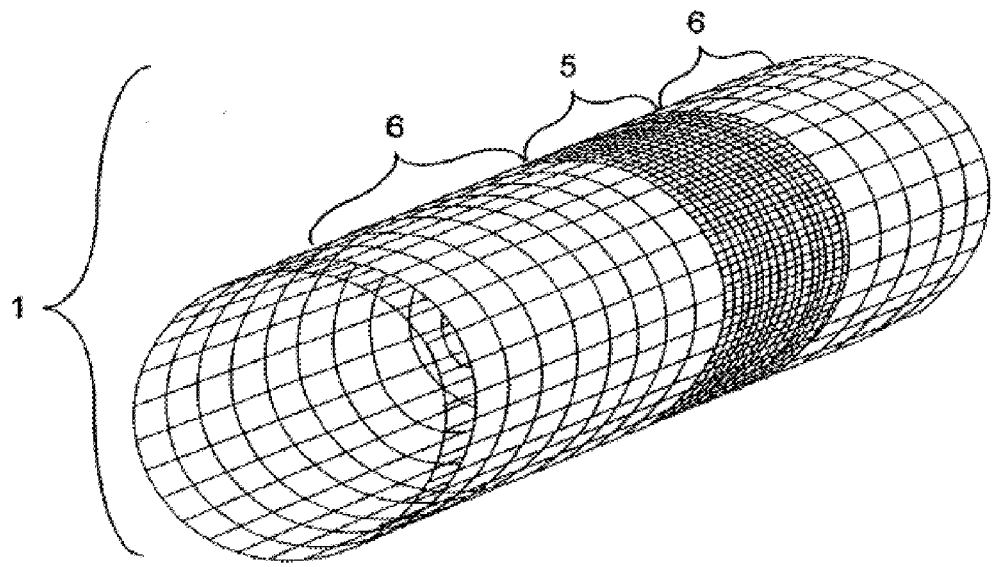

Another embodiment of the invention is illustrated in FIG. 4. In this embodiment, the sheath 1 has a central portion 5 that as decreased porosity compared to the outer portions 6 due to a varying polymer structure that makes up the material of the sheath itself. In one embodiment, the one or more polymers that make up the central portion are different (e.g., provide decreased porosity) than the one or more polymers that make up the outer portions. In another embodiment, the one or more polymers that make up the central portion are the same as the one or more polymers that make up the outer portions. In such an embodiment, the physical construction of different regions of the sheath may differ. For example, as depicted in FIG. 4, the one or more polymers may be woven or braided in a tighter manner in the central portion than in the outer portions in order to confer different porosities.

In this embodiment, the porosity of the central portion may be uniform around the entire circumference of the sheath.

Figure 5A:
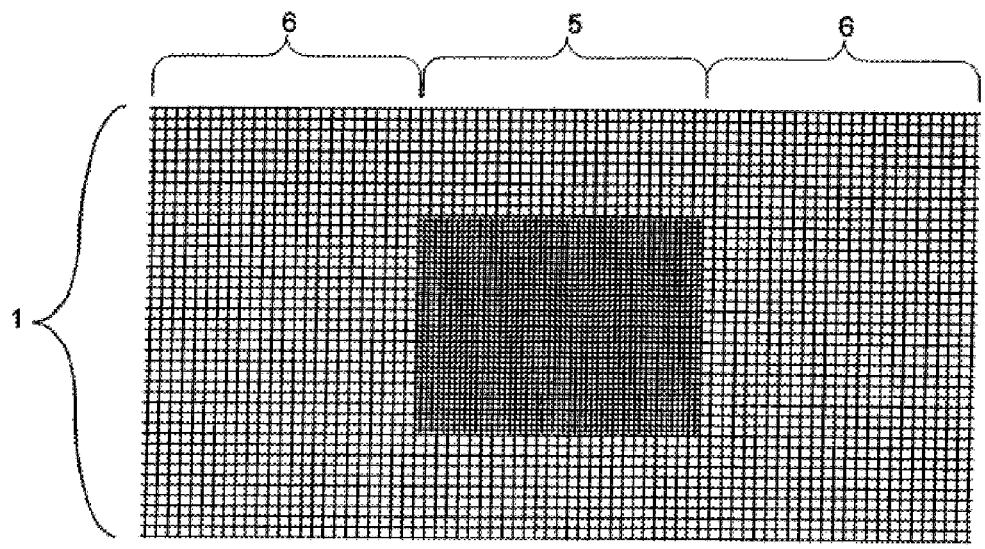
FIGS. 5A-5B are schematic views of a sheath 1 in another embodiment of the invention. In this embodiment, the porosity of the polymer structure that makes up the sheath itself is varied between the central portion 5 and the outer portions 6 of the sheath. The less permeable area of the central portion 5 is confined to a region that is smaller than the size of the middle part of the sheath. The flattened sheath in (A) has been made into a cylinder in (B). The less permeable central portion 5 does not extend around the entire circumference of the sheath as can be seen in (B).
Figure 5B:
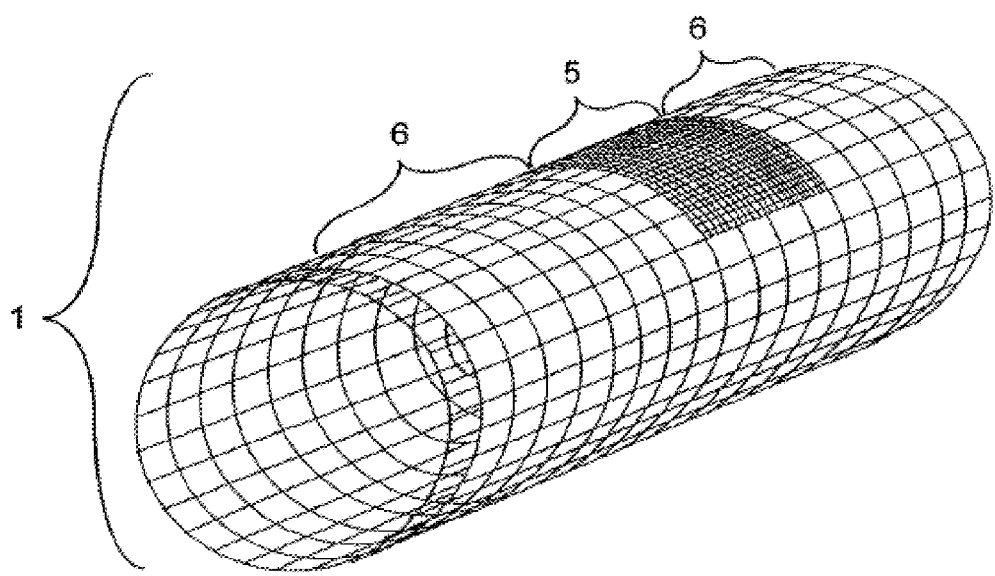

Another embodiment of the invention is illustrated in FIG. 5. In this embodiment, the sheath 1 has a central portion 5 that as decreased porosity compared to the outer portions 6 due to a varying polymer structure that makes up the material of the sheath itself as described supra for FIG. 4. Although, the porosity of the central portion 5 is overall decreased compared to the outer portions 6, the central portion does not have a uniform porosity around the entire circumference of the sheath in this embodiment. The region of decreased porosity in the central portion 5 is either made of a polymer that is different (e.g., has decreased porosity) or constructed differently (e.g., more tightly woven or braided) than the polymer that makes up the rest of sheath. This region is confined to an area that is smaller than the entire middle part of the sheath. The remainder of the middle part has a porosity that is substantially similar to that of the outer portions.

Figure 6:
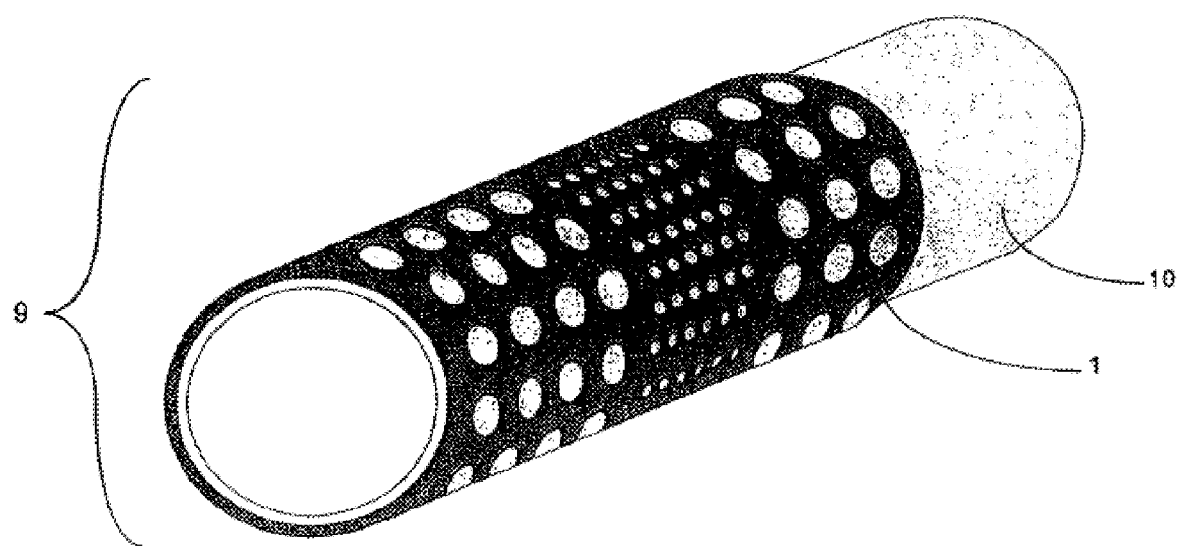
FIG. 6 is a schematic view of a sheath-covered endoprosthesis 9. The sheath 1 is shown attached to a portion of a stent 10.

FIG. 6 illustrates a schematic view of a sheath-covered endoprosthetic device 9. The sheath 1 is shown covering a portion of an endoprosthesis 10. Although the sheath shown depicts the sheath of FIG. 3, any embodiment of the sheath can be used to cover the endoprosthetic device. The sheath 1 is shown covering only a portion of the endoprosthetic device 9. In other embodiments, it may be preferable for the sheath to cover more of the endoprosthesis up to and including the entire length of the endoprosthesis.

In some embodiments, the central portion of the sheath has a uniform porosity around the entire circumference of the sheath (e.g., FIGS. 1, 2, and 4). In such embodiments, the uniform porosity of the central portion is decreased as compared to the porosity of the outer portions. In other embodiments, the region of decreased porosity is confined to an area that is smaller than the entire central portion of the sheath (e.g., FIGS. 3 and 5). The remainder of the central portion has a porosity that is substantially similar to that of the outer portions. In such embodiments, the region of decreased porosity in the central portion is present only on the side of the sheath that faces the aneurysm (e.g., one sixth, a quarter, a third, or a half of the circumference of the stent). This embodiment of a sheath-covered stent is useful when there is a perforator on the side of the vessel opposite the aneurysm that would suffer from the decreased permeability that occurs in the central portion of the sheath.

Figure 7:
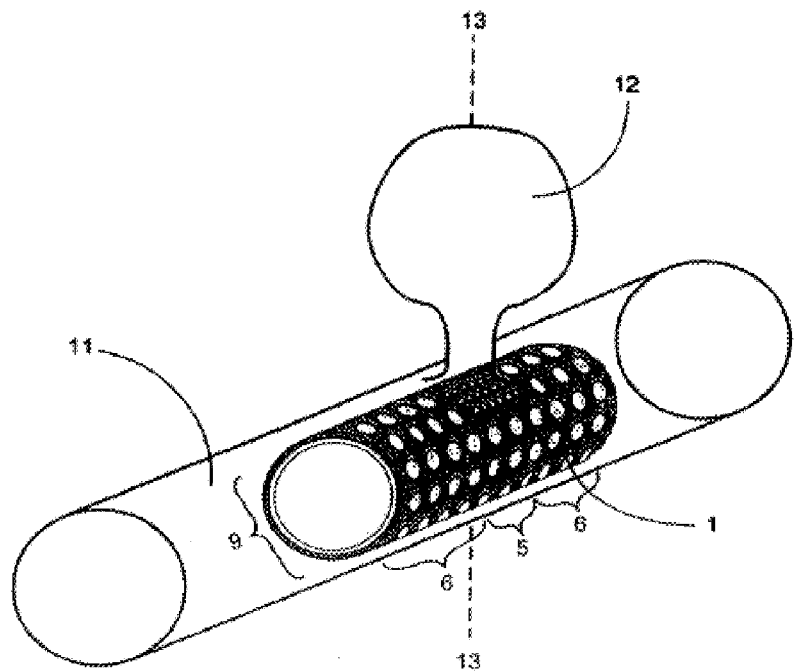
FIG. 7 is a schematic of a blood vessel with a lumen 11 with a sheath-covered endoprosthesis 9 in place facing an aneurysm 12. The central portion 5 of the sheath 1 is facing the neck of the aneurysm while the outer portions 6 of the sheath 1 are on either side of the neck of the aneurysm. The sheath-covered endoprosthesis 9 comprises a stent 10 with a sheath 1 attached.

FIG. 7 illustrates a sheath-covered endoprosthetic device 9 positioned in the lumen of a blood vessel 11 that has an aneurysm 12. The sheath-covered endoprosthesis 9 is placed inside the lumen 11 of the blood vessel by a method known in the art. The sheath-covered endoprosthesis 9 is positioned such that the central portion of the sheath 1 is facing the aneurysm 12. When placed appropriately, the central portion 5 of the sheath is facing the neck of the aneurysm while one or more outer portions 6 may be positioned beyond the neck of the aneurysm. In FIG. 7, the outer portions are positioned longitudinally distal and proximal to the neck of the aneurysm.

Any means known in the art can be used to locate the affected area (e.g., the lumen of a blood vessel or artery proximal to an aneurysm) and monitor the placement of the sheath-covered endoprosthesis. In preferred embodiments, the affected area is identified by diagnostic methods known in the art, i.e., MRI or angiography.

Figure 8:
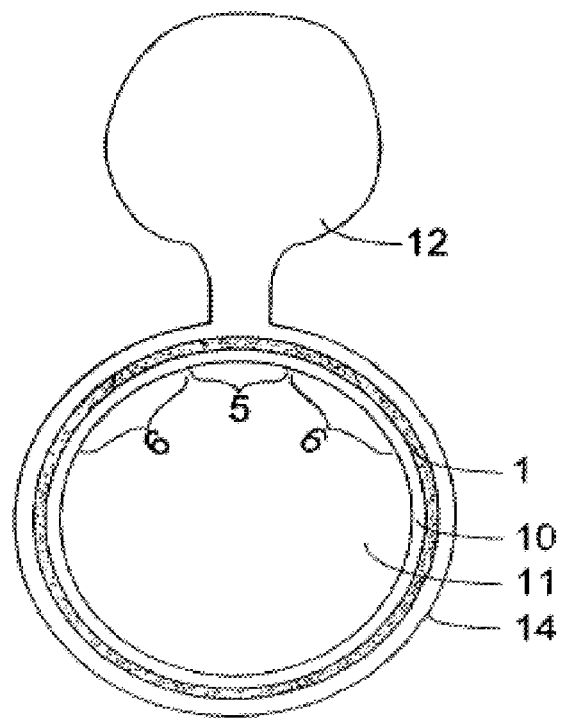
FIG. 8 is a schematic of a cross-sectional view taken through the plane designated 13 in FIG. 7 of a blood vessel 14 and an aneurysm 12 with a endoprosthetic device 10 partially covered by a sheath 1 in the vessel lumen 11. The sheath-covered endoprosthetic device is in place facing the aneurysm 12. In this embodiment, the central portion 5 of the sheath 1 is facing the neck of the aneurysm while the outer portions 6 are located circumferentially on the sides of the neck of the aneurysm. The endoprosthesis 10 and sheath 1 are adjacent to the wall of the blood vessel 14.

FIG. 8 illustrates a cross-sectional view of a endoprosthetic device 10 covered by a sheath 1 positioned in the lumen 11 of a blood vessel 14 that has an aneurysm 12. The stent 10 is positioned in the lumen 11 of the blood vessel 14 such that the central portion 5 of the sheath 1 is facing the area of the blood vessel with the aneurysm 12. In this embodiment, the central portion 5 of the sheath is facing the neck of the aneurysm while the outer portions 6 are circumferentially located on either side of the neck of the aneurysm. Thus, any perforator vessels in the proximity to the aneurism will not have their blood flow substantially impeded.

Figure 9A:
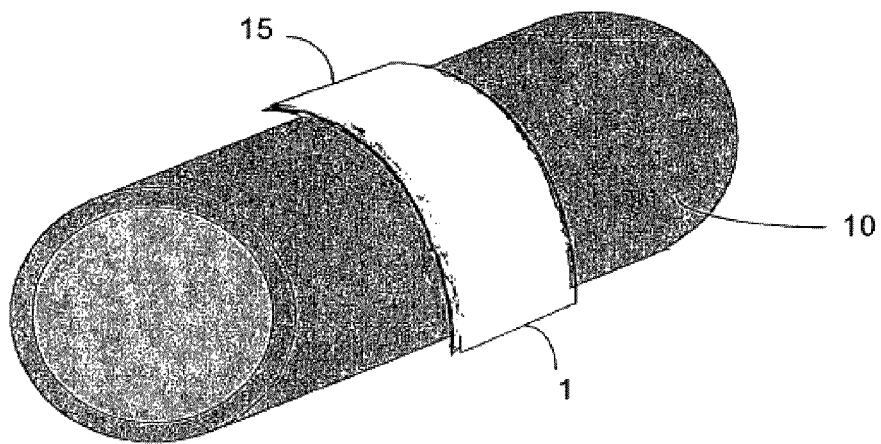
FIGS. 9A-9B is a schematic view of another embodiment of the invention where an endoprosthesis 10 that is covered by a sheath 1 embedded with a layer of material 15 that promotes endothelialization. In this schematic view (A), the sheath 1 has a central portion with no outer portions. However, a sheath of this embodiment can have outer portions that are permeable to blood flow and are not embedded with a layer of material that promotes endothelialization. In this embodiment, the porosity of the endoprosthesis 10 is varied by the preferential addition of a layer of endothelial cells on the layer of material 15 that promotes endothelialization. (B) An endoprosthesis 10 that has a polymer sheath 19 with a layer of material 15 that promotes endothelialization embedded in the central portion is depicted.
Figure 9B:
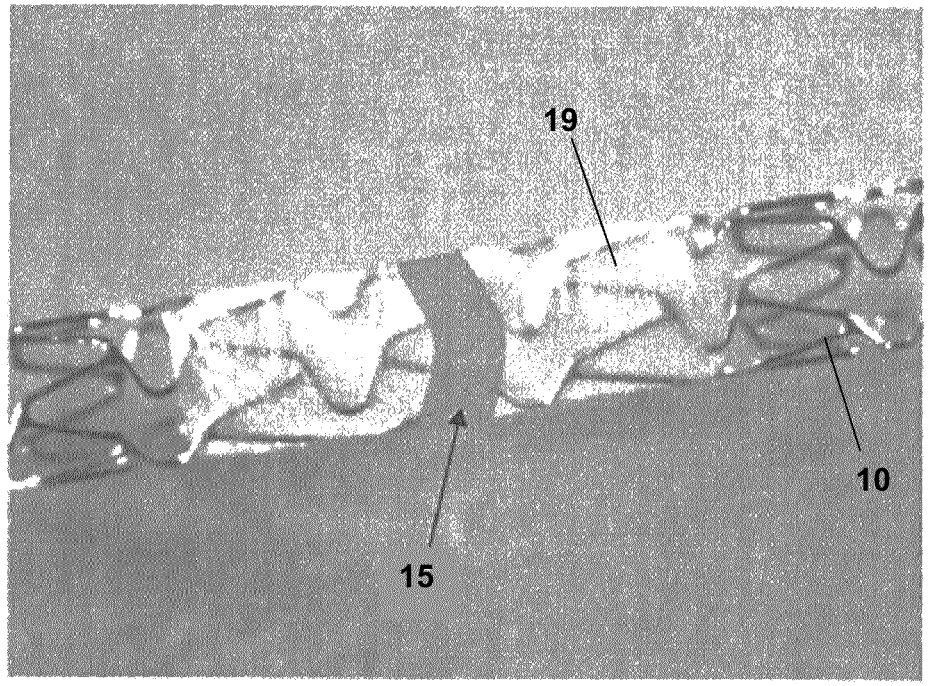

FIG. 9 illustrates an endoprosthesis 10 that is covered by a sheath 1 embedded with a layer of material 15 that promotes endothelialization. In this embodiment, the porosity of the endoprosthesis 10 is varied by the eventual preferential addition of a layer of endothelial cells on the layer of material 15 that promotes endothelialization. In some embodiments, the layer of material that promotes endothelialization can be added to a central portion of another sheath of the invention (e.g., as shown in any of FIGS. 1-5, 10 and 11) to further slow blood flow. Such an embodiment is depicted in FIG. 9B where the layer of material that promotes endothelialization is embedded in the polymer sheath of FIG. 11.

The layer of material that promotes endothelialization comprises a first molecule capable of interacting with a second molecule that is on the surface of an endothelial cell or its progenitor cell. Interactions between first and second molecules direct the endothelial cells or their progenitors to adhere to the sensor. Non-limiting examples of first molecules are antibodies or antigen binding fragments thereof, small molecules, and extracellular matrix molecules.

In one specific embodiment, layer of material that promotes endothelialization. comprises one or more antibodies or antigen binding fragments thereof. The antibody or antigen binding fragment thereof specifically binds to or interacts with an antigen on the cell membrane or cell surface of endothelial cells and/or their progenitor cells thus recruiting the cells from circulation and surrounding tissue to the sheath. The cell membrane or cell surface antigens to which the antibodies specifically bind are specific for the desired cell type (e.g., only or primarily found on endothelial cells or their progenitor cells). Several non-limiting examples of antibodies or antigen binding fragments thereof useful in the present invention are directed to the following antigens: e.g., vascular endothelial growth factor receptor-1, -2 and -3 (VEGFR-1, VEGFR-2 and VEGFR-3 and VEGFR receptor family isoforms), Tie-1, Tie-2, Thy-1, Thy-2, Muc-18 (CD 146), stem cell antigen-I (Sca-1), stem cell factor (SCF or c-Kit ligand), VE-cadherin, P1H12, TEK, Ang-1, Ang-2, HLA-DR, CD30, CD3I, CD34, CDw90, CD117, and CD133. Alternatively, cell membrane or surface antigens to which the antibodies specifically bind may not exclusively be found on the desired cell type, e.g., the cell membrane or surface antigens are found on other cells in addition to endothelial cells or their progenitor cells. In such embodiments, it may be preferable to use a mixture of antibodies that specifically bind to the non-specific cell membrane or surface antigens such that the profile of antigens recognized is unique to the desired cell type, e.g., the cell membrane or surface antigens specifically bound to by the mixture of antibodies are only or primarily found in that combination on endothelial cells and/or their progenitor cells.

In another specific embodiment, the layer of material that promotes endothelialization comprises one or more small molecules that bind one or more ligands on the cell membrane or cell surface of the desired cell. The small molecule recognizes and interacts with a ligand on an endothelial cell or its progenitor cell to immobilize the cell on the surface of the sensor to form a layer of endothelial cells. Small molecules that can be used in the methods of the invention include, but are not limited to, inorganic or organic compounds; proteinaceous molecules, including, but not limited to, peptides, polypeptides, proteins, modified proteins, or the like; a nucleic acid molecule, including, but not limited to, double-stranded DNA, single-stranded DNA, double-stranded RNA, single-stranded RNA, or triple helix nucleic acid molecules, or hybrids thereof, fatty acids; or saccharides. Small molecules can be natural products derived from any known organism (including, but not limited to, animals, plants, bacteria, fungi, protista, or viruses) or may be one or more synthetic molecules. In one embodiment, a small molecule for use in methods of the invention is a lectin. A lectin is a sugar-binding peptide of non-immune origin which binds the endothelial cell specific lectin antigen (Schatz et al., 2000, Biol Reprod 62: 691-697). In other embodiments, small molecules that have been created to target various endothelial and/or progenitor cell surface receptors can be used in the methods of the invention. For example, VEGF receptors can be bound by SU11248 (Sugen Inc.) (Mendel et al., 2003, Clin Cancer Res. 9:327-37), PTK787/ZK222584 (Drevs et al., 2003, Curr Drug Targets 4:113-21) and SU6668 (Laird et al., 2002, FASEB J. 16:681-90) while alpha v beta 3 integrin receptors can be bound by SM256 and SD983 (Kerr et al., 1999, Anticancer Res. 19:959-68).

In another specific embodiment, the layer of material that promotes endothelialization comprises one or more extracellular matrix (ECM) molecules to which endothelial cells and/or their progenitor cells naturally adhere. Examples of ECM molecules for use in accordance with the present invention are basement membrane components, such as, for example, collagen, elastin, laminin, fibronectin, vitronectin, as well as basement membrane preparations, heparin, and fibrin.

The layer of material that promotes endothelialization may optionally comprise a compound that promotes the survival, accelerates the growth, or causes or promotes the differentiation of endothelial cells and/or their progenitor cells. Any growth factor, cytokine or the like which stimulates endothelial cell survival, proliferation and/or differentiation can be used in the methods of the invention. Compounds used in the methods of the invention can be specific for endothelial cells including, but not limited to, angiogenin 1, angiogenin 2, platelet-derived growth factor (PDE-CGF), vascular endothelial cell growth factor 121 (VEGF 121), vascular endothelial cell growth factor 145 (VEGF 145), vascular endothelial cell growth factor 165 (VEGF 165), vascular endothelial cell growth factor 189 (VEGF 189), vascular endothelial cell growth factor 206 (VEGF 206), vascular endothelial cell growth factor B (VEGF-B), vascular endothelial cell growth factor C (VEGF-C), vascular endothelial cell growth factor D (VEGF-D), vascular endothelial cell growth factor E (VEGF-E), vascular endothelial cell growth factor F (VEGF-F), proliferin, endothelial PAS protein 1, and leptin. Compounds used in the methods of the invention can be non-specific for endothelial cells including, but not limited to, basic fibroblast growth factor (bFGF), acidic fibroblast growth factor (aFGF), fibroblast growth factors 3-9 (FGF 3-9), platelet-induced growth factor (PIGF), transforming growth factor beta 1 (TGFβ1), transforming growth factor alpha (TGFα), hepatocyte growth factor scatter factor (HGF/SF), tumor necrosis factor alpha (TNFα), osteonectin, angiopoietin 1, angiopoietin 2, insulin-like growth factor (ILGF), platelet-derived growth factor AA (PDGF-AA), platelet-derived growth factor BB (PDGF-BB), platelet-derived growth factor AB (PDGF-AB), granulocyte-macrophage colony-stimulating factor (GM-CSF), heparin, interleukin 8, thyroxine, or functional fragments thereof.

Figure 10:
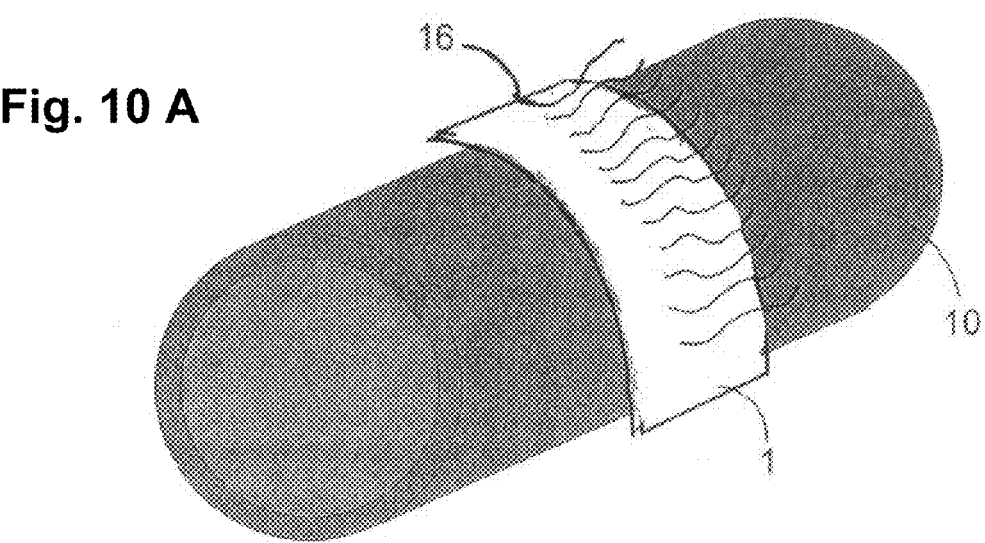
FIGS. 10A-10D show schematic views of another embodiment of the invention where an endoprosthesis 10 is covered by a sheath 1 that has projections 16. In this schematic view (A), the sheath 1 has a central portion with no outer portions. However, a sheath of this embodiment can have outer portions that are permeable to blood flow and do not have projections that promotes thrombosis. (B) A schematic of a cross-sectional view of a blood vessel 14 and an aneurysm 12 with a endoprosthetic device 10 partially covered by a sheath 1 that has projections 16 in the vessel lumen 11 is depicted. The endoprosthetic device is in place facing the aneurysm 12. In this embodiment, the projection-bearing portion of the sheath is facing the neck of the aneurysm. The projections 16 extend into the neck of the aneurysm 12 but are caught between the sheath 1 and the wall of the blood vessel 14 (and thus not extended) in areas that are not opposing the neck of the aneurysm 12. (C) An endoprosthesis 10 that has a polymer sheath 19 with projections 16 in the central portion is depicted. (D) A schematic of a blood vessel 14 with an endoprosthesis 10 that has a polymer sheath 19 with projections 16 in the central portion in place facing an aneurysm 12. In this embodiment, the projection-bearing portion of the sheath is facing the neck of the aneurysm. The projections 16 extend into the neck of the aneurysm 12 but are caught between the sheath and the wall of the blood vessel 14 (and thus not extended) in areas 17 that are not opposing the neck of the aneurysm 12. The small perforator vessels or arteries 18 in the proximity of the aneurysm are not effected by the projections.
Figure 10B:
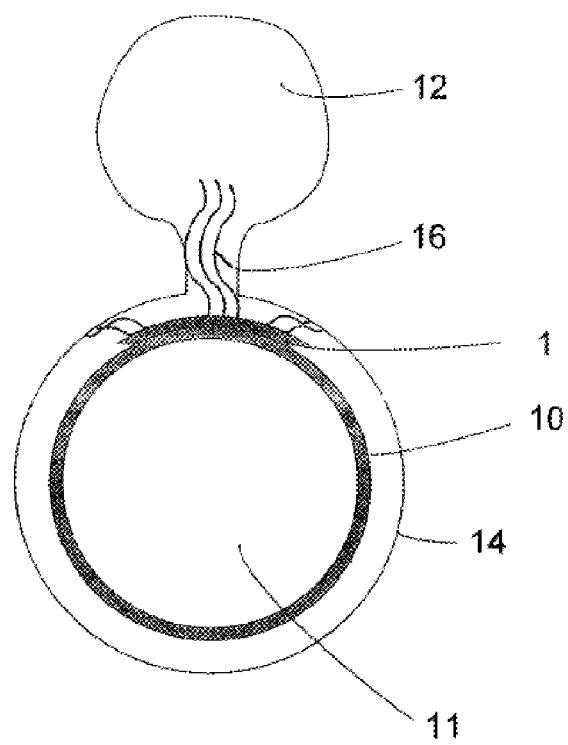
Figure 10C:
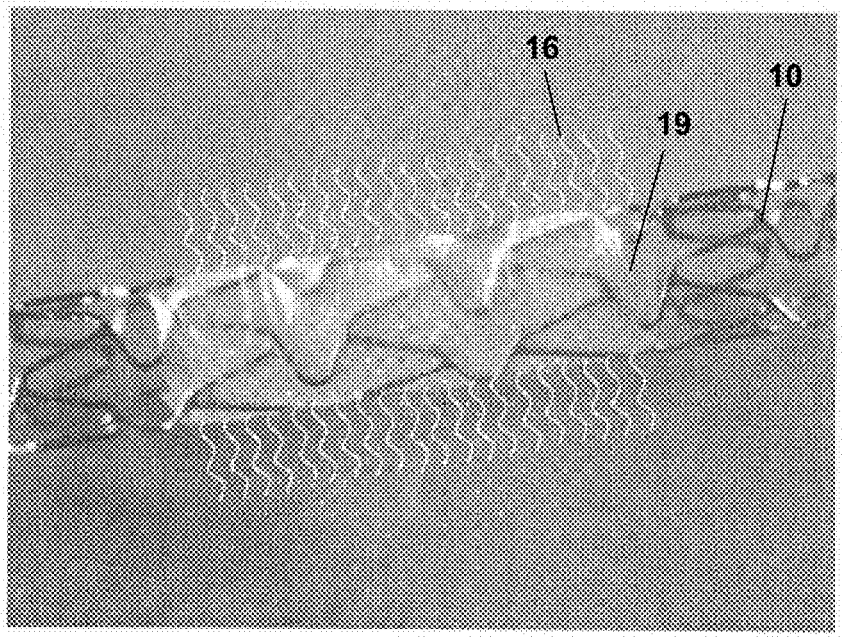
Figure 10D:
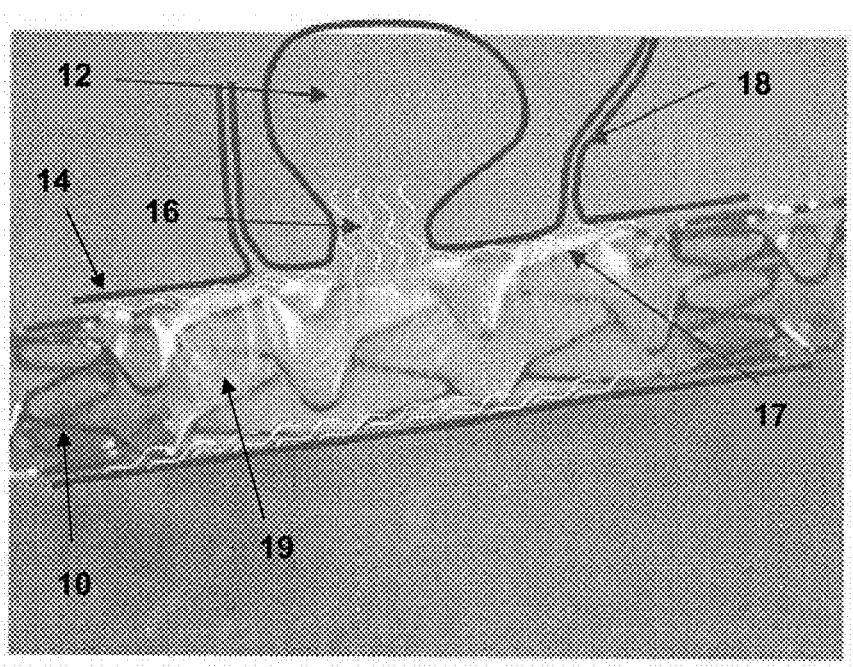

FIG. 10 illustrates endoprosthesis 10 covered by a sheath 1 that has projections 16. The projections are attached to the sheath at one end while the other end of the projection remains unattached. When placed opposite the neck of the aneurysm, the projections 16 extend into the neck of the aneurysm 12 and slow blood flow into the aneurysm. This reduced blood flow can cause a thrombosis and thus further reduce blood flow into the aneurysm. Any projections not opposite the neck of the aneurysm will not extend but be caught between the sheath 1 and the wall of the blood vessel 14. The projections preferably between 0.5-5.0 mm in length can be made of any thin, flexible material. Preferably, the projections are longer than the diameter of any perforator vessel or artery in proximity to the aneurysm. In some embodiments, the projections can be added to a central portion of another sheath of the invention (e.g., as shown in any of FIGS. 1-5, 9, and 11) to further slow blood flow. Such an embodiment is depicted in FIG. 10C where the projections are attached to the polymer sheath of FIG. 11.

Figure 11A:
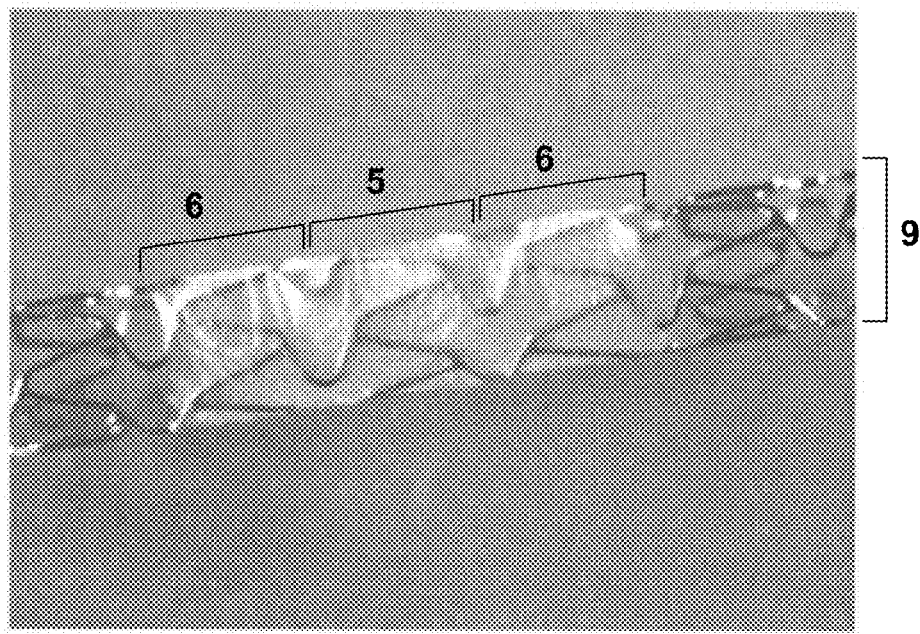
FIGS. 11A-11B are pictures of an endoprosthesis 10 covered with a sheath 1 of substantially uniform permeability to blood flow in the central 5 and outer 6 portions. The sheath 1 is made of a polymer with porosity in the range of 10-100 micrometers over its entire length. The sheath-covered endoprosthetic device 9(A) and a 500× magnification of the sheath 1(B) are shown.
Figure 11B:

FIG. 11A is a picture of an endoprosthesis 10 covered with a sheath 1 wherein the central portion 5 has substantially the same permeability to blood flow as the outer portions 6. The sheath 1 is made of a polymer that has a porosity in the range of 10-100 micrometers. Although the sheath is made of a substantially uniform material over its entire length, the properties of the perforator vessels and aneurysm themselves impart a functional difference to the sheath. Areas opposite the sheath that have an out-flow (such as perforator vessels) allow blood to flow through the sheath. Areas opposite the sheath with no out-flow (such as the aneurysm) cause blood flow to be restricted through the sheath. FIG. 11B shows a 500× magnification of the strands of the polymer that made up the sheath in this embodiment. In addition to polymers, a sheath can be made of any material capable of supporting 10-100 micrometers gaps or perforations. Optionally this sheath may, in the central portion, have an additional coating. This coating may comprise a biodegradable polymer and one or more agents which promote inflammation and/or thrombogenicity.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

What is claimed is:

1. A method of treating an aneurysm in a lumen of a vessel comprising:
    placing a sheath-covered endoprosthetic device in said lumen in the area of said aneurysm, wherein said sheath has a porosity in the range of 10-100 micrometers and a length, wherein said sheath is substantially uniformly permeable over the entirety of said length, wherein said porosity is provided by a plurality of perforations of variable size and shape; and
    positioning said sheath-covered endoprosthetic device in said lumen such that any portion of said sheath is facing said aneurysm; wherein said sheath permeability allows blood flow into areas that have an outflow but restricts blood flow into areas that do not have an out-flow.

2. The method of claim 1, wherein said endoprosthetic device is a stent.

3. The method of claim 1, wherein said aneurysm is an intracranial aneurysm.

4. The method of claim 1, wherein said aneurysm is in proximity to one or more perforator vessels or arteries and said positioning includes positioning over at least one of said perforator vessels.

5. The method of claim 1, wherein said sheath comprises a polymer having a structure and said porosity is provided by said polymer structure of said sheath.

6. A device for treating an aneurysm comprising an endoprosthetic device and a sheath, wherein said sheath is located on an external surface of said endoprosthetic device and has a porosity in the range of 10-100 micrometers and a length, wherein said sheath is substantially uniformly permeable over the entirety of said length and wherein said porosity is provided by a plurality of perforations of variable size and shape, and the resulting sheath permeability allows blood flow into areas that have an outflow but restricts blood flow into areas that do not have an out-flow.

7. The device of claim 6, wherein said endoprosthetic device is a stent.

8. The device of claim 6, wherein said sheath comprises a polymer having a structure and wherein said porosity is provided by said polymer structure of said sheath.

9. The device of claim 6, wherein said sheath comprises a central portion and outer portions, wherein only said central portion has a biodegradable coating containing one or more agents which promote inflammation or thrombogenicity.

10. The method of claim 1, wherein said sheath-covered endoprosthetic device is positioned such that a center of said sheath is located on the aneurysm.

11. The method of claim 5, wherein said sheath is formed of a plurality of strands of the polymer material.

12. The method of claim 1, wherein said perforations extend through said sheath from an endoprosthetic device-facing surface to an outer surface.

13. The device of claim 9, wherein said device is positioned such that said central portion of the sheath is located on the aneurysm.

14. The device of claim 8, wherein said sheath is formed of a plurality of strands of the polymer material.

15. The device of claim 6, wherein said perforations extend through said sheath from an endoprosthetic device-facing surface to an outer surface.

* * * * *